// 
US006843786B1

(12) United States Patent
Thuren et al.

(10) Patent No.: US 6,843,786 B1
(45) Date of Patent: Jan. 18, 2005

(54) FASTENING MEANS FOR AN ABSORBENT GARMENT

(75) Inventors: Svante Thuren, Mölnlycke (SE); Robert Kling, Skene (SE)

(73) Assignee: SCA Hygiene Products AB, Gothenburg (SE)

( * ) Notice: Subject to any disclaimer, the term of this patent is extended or adjusted under 35 U.S.C. 154(b) by 667 days.

(21) Appl. No.: 09/194,968

(22) PCT Filed: Oct. 24, 1997

(86) PCT No.: PCT/SE97/01779

§ 371 (c)(1),
(2), (4) Date: May 7, 1999

(87) PCT Pub. No.: WO98/18422

PCT Pub. Date: May 7, 1998

(30) Foreign Application Priority Data

Oct. 31, 1996 (SE) .............................. 9603973

(51) Int. Cl.⁷ ........................... A61F 13/15; A61F 13/20
(52) U.S. Cl. .................. 604/391; 604/386; 604/385.03; 604/394
(58) Field of Search ...................... 604/385.01, 385.03, 604/386, 389–396, 400–402; 2/401–408, 912–919; 602/67–73

(56) References Cited

U.S. PATENT DOCUMENTS

| | | | | |
|---|---|---|---|---|
| 3,486,501 A | * | 12/1969 | Erickson et al. ............... 602/67 |
| 3,860,003 A | * | 1/1975 | Buell ...................... 604/385.2 |
| 4,475,912 A | * | 10/1984 | Coates ........................ 604/391 |
| 4,610,682 A | * | 9/1986 | Kopp | |
| 4,773,906 A | | 9/1988 | Krushel | |
| 4,834,742 A | * | 5/1989 | Wilson et al. ............... 604/391 |
| 4,981,480 A | * | 1/1991 | Gaudet et al. ......... 604/385.26 |
| 5,151,092 A | * | 9/1992 | Buell et al. .................. 604/358 |
| 5,221,274 A | * | 6/1993 | Buell et al. .................. 604/358 |
| 5,242,436 A | * | 9/1993 | Weil et al. ............. 604/385.29 |
| 5,324,279 A | * | 6/1994 | Lancaster et al. ............. 604/39 |
| 5,330,458 A | * | 7/1994 | Buell et al. .................. 604/358 |
| 5,624,427 A | * | 4/1997 | Bergman et al. ............. 604/391 |
| 5,853,405 A | * | 12/1998 | Suprise ........................ 604/391 |

FOREIGN PATENT DOCUMENTS

| | | | |
|---|---|---|---|
| EP | 0 532 035 | 3/1993 | |
| GB | 1520740 | * 8/1978 | |
| GB | 2146230 | * 4/1985 | ................. 604/391 |
| GB | 2263224 | * 7/1993 | .............. 604/385.1 |
| GB | 2277865 | * 11/1994 | ................. 604/390 |
| WO | 92/09254 | 11/1992 | |

* cited by examiner

*Primary Examiner*—Karin Reichle
(74) *Attorney, Agent, or Firm*—Burns, Doane, Swecker & Mathis, L.L.P.

(57) ABSTRACT

An absorbent garment is provided with a first and a second waist portions joined by an intermediate region including an absorbent body. A first attachment, provided on the first waist portion, and a second attachment, provided on the second waist portion, cooperate with each other for releasable attachment. The first attachment is provided with at least two elongate attachment strip elements extending between the side edges and the second attachment is provided with an attachment strip element, oriented generally transverse to said first attachment and located at each side edge of the second waist portion. By arranging the first attachment strip elements to be separated by a distance, which is at least as large as a major proportion of the width of any one of the first attachment strip elements, and by giving each of the second attachment strips a length greater than the distance separating the first attachment strip elements, the waistband region of the garment is given good stability whilst still maintaining the advantages of adjustable reclosure.

14 Claims, 1 Drawing Sheet

FASTENING MEANS FOR AN ABSORBENT GARMENT

FIELD OF THE INVENTION

The present invention relates to an absorbent garment In particular, the invention relates to disposable absorbent garments of the type which are fastened around the user's waist, such as diapers (nappies) for both incontinence sufferers as well as for baby/infant users, and absorbent pants with waist reclosing means in particular for smaller users. Typically the garments of this invention will comprise a top sheet, a back sheet and an absorbent body therebetween.

BACKGROUND TO THE INVENTION

In the discussion of the state of the art that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

An absorbent garment is known from EP-A-0 532 035 for example. The purpose of the diaper in EP-A-0 532 035 is to provide adjustment means able to adapt to a large range of wearer sizes such that one single garment size of garment will fit a user during his/her various stages of growth. To this end, in one embodiment, two wide strips of loop material are attached onto the frontal waist portion of the garment with only a slight spacing therebetween. The width of the strips, as seen from the top edge of the garment towards the middle of the garment, is such that they occupy substantially the entire frontal waist portion, in order to fulfil their purpose.

Fastening of the diaper in EP-A-0 532 035 around the user's waist is performed by attaching strips of cooperating hook elements positioned on the inner surface of the garment (i.e. the surface of the diaper in contact with the skin) to either the top or the bottom frontal loop strip only. As disclosed, when the user is small only the lower frontal strip is used whilst the upper one is folded away inwardly inside the garment. When the user is larger, the frontal waist portion is folded out and the hook elements are to be attached to the upper frontal strip.

The slight spacing between the frontal waist strips provides better folding characteristics of the garment in the frontal waist portion to fit the various sizes of users, since it provides a convenient folding denotation (i.e. a line about which folding can take place). In an alternative embodiment, the two frontal strips can be replaced by an even wider continuous strip with no gap, although clearly no pre-defined folding denotation will be present.

The use of the wide strip portions in EP-A-0 532 035 allows adaptation to the size of a user and allows repeated reclosability of said garment. However there are serious drawbacks in that a large amount of material is required for the frontal strips in order to achieve the desired purpose. Such use of wide loop material strips constitutes a costly factor in the production of a diaper, especially when considering that the diaper of EP-A-0 532 035 is a diaper of the disposable type and that only one of the two frontal strips will be used at any one time, thus leaving the other strip obsolete. The use of the loop material in this way makes disposable diapers of this type uneconomical.

Additionally, when attempting to release one part of the attachment means (e.g. the co-acting hook element strip) from the other (e.g. the loop element) for re-adjustment or removal, the user is unable to access the area between the co-acting strips. Since the wearer, or an assistant who is fitting the garment to the wearer, cannot gain access in this way, it is not possible to apply a substantially normal (i.e. perpendicular) separating force between the two strip elements. Instead, an edge of the garment itself must be grasped proximate the location of the strip and an oblique force component applied in order to achieve separation. Not only does this mean that there must be a sufficient margin of garment material around the strip to be able to grasp it, but also the oblique force applied for separation has to be kept lower than the attachment force of the strips to the garment itself, otherwise tearing will occur. This problem can thus present significant design difficulties since a predetermined attachment force must be arranged between the cooperating strips.

The main underlying problem of the present invention relates to reducing the amount of strip attachment material which is required on the waist portion of the garment whilst providing a high degree of stability in the waist region when the front and rear waist portions are attached together. At the same time, it is important that the diaper should be adjustable to a certain range of user sizes and that the cooperating attachment strips should allow attachment and re-attachment (i.e. reclosability) when fitting.

A further problem is to provide an improved separability between the cooperating strips such that the danger of tearing of the garment is reduced.

SUMMARY OF THE INVENTION

The aforementioned problems are solved by an absorbent garment having a first waist portion opposed by a second waist portion and joined by an intermediate region suitable for the inclusion of an absorbent body for absorbing bodily exudate, each waist portion having side edges and each extending across the width of the absorbent garment. Cooperating and releaseable attachment devices are provided on the first and second waist portions. The first attachment device comprises at least two elongate first attachment strip elements between the side edges of the first waist portion. For example, the two elongate first attachment strip elements extend from one of the side edges of the first waist portion to another of the side edges of the first waist portion. The first attachment strip elements are separated over at least a part of their length by a distance at least as large as a major proportion of the width of any one of the first attachment strip elements. A second attachment strip element is located at each side edge of the second waist portion, having a major and minor length, the major length greater than the minor length and extending generally transverse to the first attachment elements. The major length of each of the second attachment strip elements is greater than the distance separating the first attachment strip elements.

The first attachment device, the elements of which are a width of a minor proportion of the length of the second attachment strip element and may be equal to, or less than, 30 mm, and the second attachment device are positioned on opposite surfaces of the garment and may be cooperating hook and loop fastening elements or cooperating cohesive adhesive strip elements. The first attachment strip elements may extend substantially across the whole distance between the edges of the first waist portion and between locations closely adjacent to where leg opening portions meet the respective side edges of the first waist portion. Additionally, the first attachment strip elements may be located substantially parallel to each other and at a distance greater than 20 mm from longitudinal centerline to centerline. An integral elongate absorbent body may extend into the first waist portion at least to a location beyond the innermost of the first attachment strip elements.

The second attachment strip elements are disposed in the second waist portion that has an outer end edge and each extend from a location proximate where a respective leg opening portion, located at the intermediate region of the absorbent garment, meets its respective side edge of the second waist portion, outwardly to a position proximate the outer end edge of the second waist portion.

BRIEF DESCRIPTION OF THE DRAWING

The objects and advantages of the invention will become apparent from the following detailed description of preferred embodiments thereof in connection with the accompanying drawings in which like numerals designate like elements and in which.

DETAILED DESCRIPTION OF PREFERRED EMBODIMENTS

Figure 1:
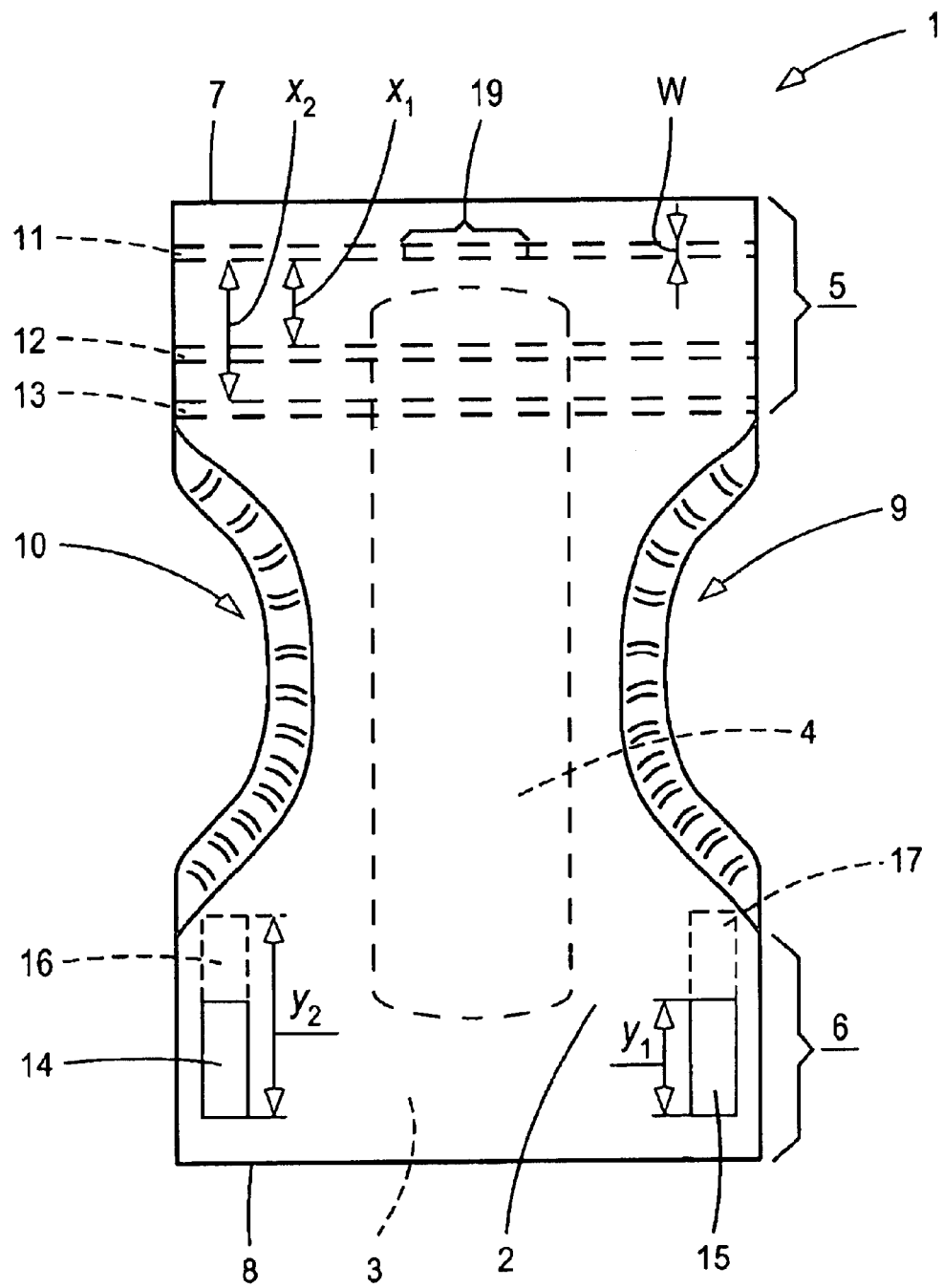
FIG. 1 shows a plan view of one embodiment of an absorbent garment according to the present invention in a folded-out condition.

With regard to the terminology used both in the claims and in the following description, a brief explanation thereof will be given below to aid the reader.

The term "waist portions" of an absorbent garment refers to the general areas at either end of the absorbent garment which are designed such that, when fitted to a user, they will be proximate to the front and rear portions of the user's waist. The waist portions will often be provided with elastication means. In a diaper, these front and rear waist portions will start at an outer longitudinal edge of the diaper and extend towards the middle of said diaper by a certain distance, typically between 30 mm (typical in very small diapers) up to about 120 mm in adult incontinence diapers. The two waist portions will be joined by an intermediate region, the side edges of which are typically substantially taken up by leg-opening portions which may be elasticated. A typical ratio of proportions in a diaper is such that the extent of the waist portion inwardly towards the middle of the diaper constitutes between about 20% to 40% of the whole diaper length. Expressed in other terms, the extent of the frontal waist portion, when a correct size diaper is fitted correctly on a wearer, can be seen as approximating to the distance from the upper edge of the diaper, when fitted, to the top of the user's thighs.

Additionally it is to be understood that the absorbent garments of the present invention may include an absorbent body, or member, as an integral part thereof, or that they may be of the type where an absorbent body or absorbent member is added. The latter type may, for example, be of the type where a garment is formed of two waist regions and an intermediate body with an absorbent body but where the absorbent body or element is removable such as in the case where the same absorbent garment is to be used several times with a replaceable absorbent body.

The first and second attachment means are defined as cooperating with each other for releasable attachment. By this it is meant that each of said first and second attachment means has a surface which will releasably engage the respective opposed attachment means. A preferred form of this in the present application would be hook and loop fastening means (known per se), whereby an attachment strip having hook members is disposed integrally with, or on, one waist portion of the garment and an attachment strip having loop members would be disposed integrally with, or on, the other waist portion. Hook and loop fastening means are merely an example of what are known generally in this technical field as releasably attachable fastening means and more particularly as releasably attachable mechanical fastening means. The hook and loop attachment means thus provide mechanically interengaging, or in other words mechanical cooperation, between each other. An example of such mechanical fastening means is for example sold under the trademark VELCRO. Various types of releasably attachable mechanical fastening means are known in this field and are to be understood as included within the definition of attachment means for releasable attachment. Thus where hook and loop elements or strips are referred to it is equally applicable to use other releasable mechanical fasteners of this type.

In certain situations hook and loop members may both be used on either one or both surfaces. In a further embodiment of said cooperating attachment means, the strips may be constituted by portions of the absorbent garment having cohesive adhesives applied thereto. Such cohesive adhesives are particular in that they do not exhibit a large adhesive capacity to any surface apart from a surface having a cooperating cohesive adhesive component thereon.

The expression "generally transverse" as used to define the lay of the strips of the first and second attachment means, is intended to mean that the strips of one attachment means, in terms of how they are positioned with respect to the diaper in a folded-out, generally flat condition, lie generally perpendicularly to the strips of the other attachment means, within certain limits of about ±20° for example.

The expression "minor proportion" refers to a proportion which is less than 50% of the reference measurement. For example, a minor proportion of 10 is less than 5. A "major proportion" refers to a proportion which is greater than 50% of the reference measurement.

The terms "width" and "length" are used in various ways in the following. When reference is made to the first attachment strip elements, the length refers to the dimension as seen in a direction transverse to the longitudinal axis of the absorbent garment; the longitudinal axis of the absorbent garment being the axis extending between the middle of each of the two waist portions. Conversely, the width of the first attachment strip elements refers to their dimension as seen in a direction generally parallel with the longitudinal axis of the garment. In respect of the second attachment means, "length" refers to their dimension in the general direction of the longitudinal axis of the garment whereas their width is their dimension transverse to this.

Additionally, and in particular with regard to the use of cohesive adhesive attachment strip elements, a single strip element may be constituted by very fine strips of attachment material (e.g. cohesive adhesive) applied as a set of very closely adjacent intermittent or continuous rows. In such a case, the width of the attachment strip element is to be understood as the distance between the outer margins of said closely adjacent set of rows comprised in one strip element. For example, a single attachment strip element may be comprised of three rows of cohesive adhesive applied with a width of e.g. 4 mm and separated by a distance of e.g. 2 mm. In such a case, the width of the attachment strip element would be 4+2+4+2+4=16 mm.

Where a similar attachment strip element with the same width (i.e. 16 mm) is then used in order to constitute the further strip element of the attachment means, the spacing between the two attachment strip elements must be of the order of at least 8 mm and preferably 20 mm or more.

Where different widths of attachment strip elements are present in the two (or more) attachment strip elements, such as 16 mm and 20 mm for example, the spacing between the strip elements must be at least 8 mm, and preferably 20 mm or more.

The disposable absorbent garment 1 depicted in FIG. 1 shows the inner side of the garment (i.e. the side of the garment contacting the user's skin during use). The inner layer or liner 2 (which may form all, or part, of the inner layer) will preferably be made of a PP material such as a consolidated spunbonded polypropylene sheet which is treated so as to be permeable to fluids. The backsheet 3 will preferably be constituted by a fluid-impermeable film material such as PE or PET in a conventional manner. Other suitable materials may of course be used for the various layers. Additionally, other sheets or layers may be added inbetween the sheets 2 and 3. Between the two sheets there is an absorbent body 4, typically of cellulose pulp fibres or the like, optionally containing one or more SAP components for example.

The garment 1 has two waist portions, preferably elasticated, at either end thereof. A first waist portion 5 is positioned at one end of the article and a second waist portion 6 is positioned at the other end of the article. As can be seen, in this embodiment, the waist portion 5 is the part of the garment extending from one end 7 (i.e. the upper edge) of the garment to a location approximately level with the locations where the leg openings 9 and 10 meet the longitudinal side edges close to the top of the garment, said waist portion extending across the width of the article. Similarly the second waist portion 6 extends from the end 8 (i.e. the lower edge) of the garment to a location approximately level with the locations where the leg openings 9 and 10 meet the longitudinal side edges close to the bottom of the garment, said waist portion also extending across the width of the article. Depending on the type of absorbent garment which is used, the exact extent of the first and second waist portions will vary. Moreover, the waist portions are preferably similar or equal in length, but this is not a requirement. Asymmetric garments may be used for example.

Three first attachment strip elements 11, 12 and 13, shown in the drawing as continuous attachment strips having a constant width w and being disposed across the first waist portion 5, constitute the first attachment means. A preferred width of the first attachment strip elements is equal to, or less than, 30 mm. This width is a minor proportion of the length of the second attachment strip elements. In a preferred embodiment only two attachment strip elements are required, although more strip elements may be used. However, at least two strip elements must be used according to the invention. For example only strip elements 11 and 12, or strip elements 11 and 13 might be required.

The strip elements are shown as hidden detail since they are disposed on the outer side of backsheet 3, not visible in this Figure. Each of the strip elements 11, 12 and 13 preferably comprises a strip of loop material. Each of said strip elements is furthermore elongate such that the width of each strip element is a minor proportion of its length, and preferably a very minor proportion of its length, such as for example about 5%.

The strip elements 11, 12, 13 extend between the side edges of the first waist portion 5. However, it is not required that they extend with each end positioned exactly coterminous with a respective side edge of the waist portion. A clearance may be provided such that the end of the respective strip element is positioned inwardly of the waist portion side edge. The clearance may be sufficient merely to allow for manufacturing tolerances if longitudinal production techniques are used, or the clearance may be larger.

The distance, $x_1$ or $x_2$ for example, between the facing edges of the strip elements is a distance which is at least as large as a major proportion of the width of any of the strips 11, 12, or 13 over at least part of their length and preferably the whole of their length. In most cases this distance will be considerably larger, such as three or four times larger. The distance between the strip elements will preferably be at least about 14 mm and normally more. However, the minimum distance between the centrelines of adjacent single strip elements should be greater than 20 mm. If a finger is to be fully inserted under the outer strip element, said distance may be chosen to be larger (e.g. 35 to 40 mm or more). The purpose of this dimensioning will be explained in more detail below. In a further embodiment a central portion 19, and/or other portions, of one or more of the strip elements 11, 12, or 13 may be omitted so as to form a discontinuous strip element.

Disposed on the second waist portion 6, proximate the side edges thereof and on the inner side of said garment, are at least two second attachment strip elements 14 and 15 extending generally parallel to the direction of the garment's longitudinal axis and generally transverse to said first attachment strip elements. In some cases the strip elements 14 and 15 may be somewhat slanted with respect to said longitudinal direction and can present a somewhat diverging or converging relationship. Further strip elements 14 and 15 may also be used, although in a preferred embodiment using hook and loop attachment means only two are needed.

Said strip elements 14 and 15 are positioned proximate the outer edges of said second waist portion, but preferably a short distance (e.g. 5 mm to about 20 mm) inside said outer edges. The second attachment strip elements 14 and 15 comprise hook material strips (presuming that the first attachment strips comprise loop material) which will cooperate with the first attachment strip elements for releasable attachment thereto.

The strip elements 14 and 15 extend from a location proximate the end 8 of the garment preferably up to a location close to the inner end of the waist portion. In the Figure, such strip elements which correspond to said definition are illustrated by the extensions 16 and 17 of strip elements 14 and 15 respectively. The use of dotted lines merely indicates a possible extension of said strip elements 14 and 15 and is not intended to show hidden detail.

Each of strip elements 14 and 15 is preferably the same length $y_1$. The length $y_1$ will normally vary depending on the size of the absorbent garment, but will typically be in the range of between about 15 mm up to about 100 mm. The length $y_1$ of the strip elements 14 and 15 is however dependent on the spacing between said first attachment strip elements 11, 12, and 13. Thus, taking the preferred embodiment with only two uniform width strip elements 11 and 12 separated by a distance $x_1$, which in this case is substantially constant, the length $y_1$ of the strip elements 14 and 15, in accordance with the invention, must be greater than $x_1$. This relationship must apply over at least part of the length of the strip elements 11–13. In most cases, the relationship should apply over the whole length of the first attachment strip elements. However, said relationship might apply only at the outer portions of the strip elements 11–13, where it would normally be expected that the second attachment strips would be fastened. A divergence from the claimed relationship at other parts along the length of the first strip elements may for example be to accommodate angling of the second attachment strips if required. Angling of the attachment strips 14 and 15 upon attachment to strip elements 11–13 will be described in more detail below.

Preferably, the length of each of strip elements 14 and 15 will be approximately equal to the distance between said two first attachment strip elements in addition to the width w of each of said first attachment strips. Thus, the strips 14 and 15 may have a length $y_1 = x_1 + 2w$.

In an even more preferred embodiment the length of strips 14 and 15 will have a length $y_1$ greater than $x_1 + 2w$ over at least part of their length and preferably the whole of their length. Such an embodiment allows slanting or angling of the strips elements 14 and 15 when attaching these to the cooperating strip elements. Such angling will be explained in more detail below with respect to comfort requirements.

However, the length $y_1$ in relation to the distance $x_1$ (or $x_2$) can readily be determined by a skilled man in accordance with the materials used and their exact dimensions. For example it may be only necessary to arrange length $y_1$ to be equal to $x_1 + w$, or less in some cases.

Where two strip elements 11 and 13 are used, distance $y_2$ (length of strips 16 and 17) will be at least as large as distance $x_2$ if only two strips 11 and 13 are affixed on said first waist portion.

If three or more strip elements 11, 12, 13 are used, the distance of separation between the first attachment strip elements is to be understood as the distance between the inner edges of the two outermost strip elements 11, 13 at the part of their length in question.

Additionally, the strip elements may have rounded outer ends (not shown). In such a case, the distance between the strip elements 11, 12, 13, or similarly their width dimensions, is to be understood as excluding said rounded end portions.

All of the strip elements 11–17 should be kept to a minimum width so as to achieve maximum material savings whilst maintaining the advantages of waist stability which will be explained below. Thus preferably none of the strip elements should have a width greater than about 30 mm. More preferably the width will be even less, of the order of 15 mm or less for example. Additionally, the strip elements may have different widths such as, by way of example only, 20 mm for one strip and 24 mm for another of said strip elements. Moreover it is possible to vary the width of a strip element along its length such that it will have varying widths at different locations therealong. However the relationship defined in the claims must apply at least over a part of the length of the strip elements at two locations, one on either side of the longitudinal centreline of the garment. In the preferred embodiment however, each of the strip elements will have a substantially constant width along its whole length.

Waist stability refers to the maintenance of the waist portions, particularly the front waist portion, in a generally non-sagging relationship in the fitted position of the garment. In order to provide good waist stability attachment of the front and rear waist portions of the diaper should be provided at spaced locations which are proximate the upper and lower parts of the waist portions. Without waist stability, the garment feels uncomfortable, especially in larger users, and over-tightening of some prior art diapers is often the result, which is both uncomfortable and does not fully solve the stability problem. Waist stability is however achieved in this invention by the two strip elements 14 and 15 being attached, at respective ends of each strip element, to both the upper and lower first attachment strips 11 and 12 for example. Said attachment occurs after fitting the garment between the user's legs and folding the edges of the waist portion 6 around the backsheet at the front waist portion 5. Since the strip elements 14 and 15 have been dimensioned to span this relatively large distance $x_1$, each of the strip elements provides support at at least two separate, relatively large-spaced locations which provides the required stability. Significant costs are thus saved compared to one wide first attachment strip or two, wide closely-adjacent strips of the prior art, all without losing any stability in the waist portions and generally providing an improvement therein. As will also be apparent, the garment of this invention does not sacrifice the advantages of releasable attachment or adjustability for varying user sizes.

Additionally, when the spacing is in the defined relationship, and particularly with a large separation distance, it is clear that said separation distance allows an assistant, or the wearer, to be able to separate the cooperating attachment strip elements by inserting a finger or a part of a finger under the strip element lying on top (in the fitted state of the garment) of the cooperating strip element (i.e. at a location between the facing inner margins of the first attachment strip elements 11–13 and between either one of the second attachment strip elements and the surface layer with which said first attachment strips are integrated).

By means of the invention, variations in fitting the cooperating first and second attachment means together may be achieved by the fitter of the garment (normally the wearer, if the wearer is a capable adult or older child, but sometimes a nurse or other helper such as a child wearer's parent) slanting the attachment strip elements 14 and 15 so that they lie at an angle other than 90° to the first attachment strips (e.g. at 70°). In this way, for some wearers, better fitting of the garment is effected since their body dimensions or comfort requirements in the upper and lower parts of the waist portions may be different. Due to the slanted fitting at upper and lower sections of the waist portion the upper part can be made looser than the lower part, or vice-versa.

The absorbent core is shown as extending into the front waist portion (the first waist portion 5 in the embodiment shown). Since the first attachment strip elements 11, 12, 13 are themselves normally attached to the back sheet, rather than being part of it, attachment to this area when an absorbent core has already been inserted in the production process results in it being more difficult to attach a very wide strip element. By the use of thinner strip elements as in the present invention, which are spaced as defined, the strip elements are more easily able to be attached securely to the back sheet since they adapt more easily to the shape and stiffness variations in the garment which may be present at that location.

Whilst the preferred embodiment of this invention relates to hook and loop materials being used for the attachment means, it is also envisaged that strips of cooperating cohesive adhesives may be used instead. In this way, the advantages of belt stability are maintained whilst the releasable attachment and adjustability advantages also remain, since the cohesive adhesive which will form strip elements 14 and 15 will not attach readily to the back sheet. Such cohesive adhesives are generally applied in the form of a film to the required surfaces and one disadvantage thereof is that they reduce the "breathability" of the product in the areas where they are applied. Consequently, when this invention is used by employing cohesive adhesives, the breathability of the product is only marginally affected due to the minimum surface area coverage along the two relatively thin first and second attachment strip elements required for maintaining stability.

The invention has been described above with reference to certain preferred embodiments possible within the claims. However such embodiments are not to be seen as limiting for the invention and the claims are to be understood in their full scope. For example, whilst shown as straight and parallel the first attachment strips may be formed as strip elements which are curved and/or convergent and/or divergent from one side edge of the garment to the other, with or without a small gap 19 therebetween. Further modifications and variations within the scope of the invention will become apparent to the reader. Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. An absorbent garment comprising first and second waist portions at opposed ends thereof, the waist portions each having side edges, wherein the waist portions are joined by an intermediate region suitable for the inclusion of an absorbent body for absorbing bodily exudate, and wherein a first attachment device is provided on the first waist portion, and a second attachment device is provided on the second waist portion, the first and second attachment devices cooperating with each other for releasable attachment, wherein the first attachment device comprises at least two elongate first attachment strip elements extending between the side edges of the first waist portion and the second attachment device comprises a second attachment strip element at each side edge of the second waist portion, each of the second attachment strip elements having a major and a minor length, the major length greater than the minor length and the major length extending generally transverse to the first attachment strip elements, wherein the first attachment strip elements are separated, over at least a part of their length, by a distance which is at least as large as a major proportion of the width of any one of the first attachment strip elements as measured at the at least a part of their length, and in that the major length of each of the second attachment strip elements is greater than the distance separating the first attachment strip elements.

2. The absorbent garment according to claim 1, wherein the width of each of the first attachment strip elements is a minor proportion of the length of the second attachment strip elements.

3. The absorbent garment according to claim 1, wherein the first and the second attachment devices comprise cooperating hook and loop fastening elements.

4. The absorbent garment according to claim 1, wherein the first and the second attachment devices comprise cooperating cohesive adhesive strip elements.

5. The absorbent garment according to claim 1, wherein the first attachment device is provided on a first surface of the garment and the second attachment device is provided on an opposite surface, such that the attachment devices are provided on the inside and outside surfaces of the garment, respectively.

6. The absorbent garment according to claim 1, wherein the width of each of the first attachment strip elements is equal to, or less than, 30 mm.

7. The absorbent garment according to claim 1, wherein the distance ($x_1+w$) between the longitudinal centrelines of the elongate first attachment strip elements of the first attachment device is greater than 20 mm.

8. The absorbent garment according to claim 1, further comprising an absorbent body, wherein the absorbent body is integral with the garment, and the absorbent body is elongate and extends into the first waist portion at least to a location beyond the innermost of the first attachment strip elements, as seen with respect to the middle of the garment.

9. The absorbent garment according to claim 1, wherein the intermediate region of the absorbent garment comprises two leg opening portions, and the innermost one of the first attachment strip elements extends between locations closely adjacent where the leg opening portions meet the respective side edges of the first waist portion.

10. The absorbent garment according to claim 1, wherein the second waist portion has an outer end edge and wherein the intermediate region of the absorbent garment comprises two leg opening portions, and the second attachment strip elements each extend from a location proximate where a respective leg opening portion meets its respective side edge of the second waist portion, outwardly to a position proximate the outer end edge of the second waist portion.

11. The absorbent garment according to claim 1, wherein the first attachment strip elements extend substantially across the whole distance between the edges of the first waist portion.

12. The absorbent garment according to claim 1, wherein the first attachment strip elements extend across the whole distance between the edges of the first waist portion, allowing for manufacturing tolerances.

13. The absorbent garment according to claim 1, wherein the at least two elongate attachment strip elements of the first attachment device are disposed substantially parallel to each other.

14. An absorbent garment comprising first and second waist portions at opposed ends thereof, the waist portions each having side edges and each of the waist portions extending across a width of the absorbent garment, wherein the waist portions are joined by an intermediate region suitable for the inclusion of an absorbent body for absorbing bodily exudate, and wherein a first attachment device is provided on the first waist portion, and a second attachment device is provided on the second waist portion, the first and second attachment devices cooperating with each other for releaseable attachment, wherein the first attachment device comprises at least two elongate first attachment strip elements extending from one of the side edges of the first waist portion to another of the side edges of the first waist portion and the second attachment device comprises a second attachment strip element at each side edge of the second waist portion, each of the second attachment strip elements having a major and a minor length, the major length greater than the minor length and the major length extending generally transverse to the first attachment strip elements, wherein the first attachment strip elements are separated, over at least a part of their length, by a distance which is at least as large as a major proportion of the width of any one of the first attachment strip elements as measured at the at least a part of their length, and in that the major length of each of the second attachment strip elements is greater than the distance separating the first attachment strip elements.

* * * * *